(12) United States Patent
Zhu et al.

(10) Patent No.: US 9,362,108 B2
(45) Date of Patent: Jun. 7, 2016

(54) SILICON NANOWIRE BIO-CHIP STRUCTURE

(71) Applicants: Jianjun Zhu, Shanghai (CN); Yulan Zhao, Shanghai (CN); Hongbo Ye, Shanghai (CN); Jiming Qi, Shanghai (CN)

(72) Inventors: Jianjun Zhu, Shanghai (CN); Yulan Zhao, Shanghai (CN); Hongbo Ye, Shanghai (CN); Jiming Qi, Shanghai (CN)

(73) Assignees: SHANGHAI IC R&D CENTER CO., LTD, Shanghai (CN); EAST CHINA NORMAL UNIVERSITY, Shanghai (CN)

( * ) Notice: Subject to any disclaimer, the term of this patent is extended or adjusted under 35 U.S.C. 154(b) by 0 days.

(21) Appl. No.: 14/439,228

(22) PCT Filed: Nov. 21, 2012

(86) PCT No.: PCT/CN2012/084941
§ 371 (c)(1),
(2) Date: Apr. 28, 2015

(87) PCT Pub. No.: WO2014/067185
PCT Pub. Date: May 8, 2014

(65) Prior Publication Data
US 2015/0276666 A1    Oct. 1, 2015

(30) Foreign Application Priority Data
Nov. 1, 2012  (CN) .......................... 2012 1 0431190

(51) Int. Cl.
*H01L 21/02* (2006.01)
*H01L 29/16* (2006.01)
*H01L 21/3065* (2006.01)
*H01L 29/06* (2006.01)
*G01N 27/414* (2006.01)

(52) U.S. Cl.
CPC ...... *H01L 21/0214* (2013.01); *H01L 21/02164* (2013.01); *H01L 21/02238* (2013.01);
(Continued)

(58) Field of Classification Search
CPC . H01L 29/58; H01L 29/0692; H01L 29/0673; H01L 29/66083; H01L 29/66439
USPC .......................................................... 257/253
See application file for complete search history.

(56) References Cited

U.S. PATENT DOCUMENTS

| 6,204,517 B1 * | 3/2001 | Wu | ........................ | B82Y 10/00 |
| | | | | 257/204 |
| 8,022,408 B2 * | 9/2011 | Cho | ........................ | B82Y 10/00 |
| | | | | 117/4 |

(Continued)

FOREIGN PATENT DOCUMENTS

| CN | 102437190 A | 5/2012 |
| CN | 102980920 A | 3/2013 |

*Primary Examiner* — Phuc Dang

(57) ABSTRACT

A silicon nanowire bio-chip structure and a manufacturing method thereof. The structure comprises a semiconductor substrate (1), a $SiO_2$ insulating layer (2) formed on the semiconductor substrate, a polysilicon layer (3) formed on the $SiO_2$ insulating layer (2) and a structural layer formed on the polysilicon layer (3); wherein, the polysilicon layer (3) comprises a patterned silicon nanowire array (4); the structural layer includes a SiON layer, a TaN and/or $Ta_2O_5$ layer (6) from bottom to top, the TaN and/or $Ta_2O_5$ layer only covers surface of each silicon nanowire in the silicon nanowire array. The silicon nanowire array is prevented from being polluted during preservation and use, and the pollutants of Na ions, K ions, Fe ions, Cu ions and Ca ions as well as the effects of chemical factors including the PH value are blocked during biological detection, thereby achieving the high stability of detection.

5 Claims, 4 Drawing Sheets

(52) U.S. Cl.
CPC ........ *H01L21/3065* (2013.01); *H01L 29/0673* (2013.01); *H01L 29/16* (2013.01); *G01N 27/4145* (2013.01); *G01N 27/4146* (2013.01); *H01L 21/02488* (2013.01); *H01L 21/02532* (2013.01); *H01L 21/02595* (2013.01); *H01L 21/02603* (2013.01)

(56) References Cited

U.S. PATENT DOCUMENTS

| | | | |
|---|---|---|---|
| 2010/0252810 A1* | 10/2010 | Fuller | H01L 21/32137 257/14 |
| 2013/0102134 A1* | 4/2013 | Jing | B82Y 10/00 438/478 |

* cited by examiner

SILICON NANOWIRE BIO-CHIP STRUCTURE

CROSS-REFERENCE TO RELATED APPLICATION

This application claims the priority benefit of International Patent Application Serial No. PCT/CN2012/084,941, filed Nov. 21, 2012, which is related to and claims the priority benefit of China patent application serial no. 201210431190.3 filed Nov. 1, 2012. The entirety of each of the above-mentioned patent applications is hereby incorporated by reference herein and made a part of this specification.

FIELD OF THE INVENTION

The present invention relates to the field of bio-chip manufacturing and particularly to a silicon nanowire bio-chip structure and a manufacturing method thereof.

BACKGROUND OF THE INVENTION

Nowadays, treatment for human health-threatening diseases such as diabetes, cardiovascular disease, respiratory disease, liver disease and cancer still progress slowly although medicine and related science continue to advance. The reasons why such diseases cannot be detected early include that on the one hand, early signs of these diseases are unobvious and protein factors uniquely secreted by disease cells are too few to be inspected by the conventional detecting means; on the other hand, even if the protein factors can be detected, it is both costly and time-consuming. Therefore, it is of profound significance to develop a highly sensitive, fast and low-cost disease sensor for human health-threatening disease treatment.

Generally, disease sensors used in industry are electrochemical sensors, optical sensors, FET sensors based on nanotechnology, or the combination thereof. The technology of electrochemical sensors is comparatively mature, but it places highly demands on solution condition and requires large volume. Moreover, to any kind of disease, the disease-related molecules are various and probably independent to each other, thus joint detection should be performed to the various disease-related factors for accurate disease detection. However, the conventional disease sensors can merely detect for a single target molecule. By contrast, FET sensors based on silicon nanowire (SiNW) array and utilizes field effect transistors to achieve signal collection and signal amplification can detect the target signals more effectively.

For example, the Chinese patent application no.CN200910030342.7 discloses a manufacturing and integrating method of a highly sensitive multi-channel bio-sensor. Compared with the conventional detectors, the FET sensor based on silicon nanowire array has the following advantages:

1). high sensitivity: firstly, the field-effect transistor itself has signal amplification function which can amplify small amount of charges applied thereon; secondly, the nanowire has large specific surface area and quantum confinement effect, which can increase the sensitivity of the FET sensor based on nanowire array;

2). fast detection speed: the detection speed of the FET sensor based on silicon nanowire array can reach GHz frequencies, which is much higher than that of the conventional sensors;

3). easy integration and high throughput detection: compared with the conventional sensors and detectors, the FET sensor based on silicon nanowire array has the advantages of easy integration and low cost; since the FET sensor can be manufactured by standard semiconductor fabrication process, the manufacturing process of the FET sensor is compatible with the semiconductor technology and the emerging MEMS technology, thereby achieving sensing with rich function and superior performance.

However, for structures based on silicon nanowire array, during the process of technology research and application, there still exists problems to be solved:

1). vulnerable to pollution in preservation and in use: since the silicon nanowire array has high surface sensitivity, merely forming a $SiO_2$ passivation layer (as mentioned in CN200910030342.7) is hard to prevent the pollutants of Na ions and K ions or to block the effect of environmental factors such as PH value and humidity; accordingly, the sensor chip is greatly affected by the salt content, the PH value and the humidity of the environment and is difficult to be preserved or transported;

2). performance instability in use: in biological detection, due to the diversity of bulk and solution of the samples, the chip sensor may also be subjected to spread pollutants such as Na ions, K ions, Fe ions, Cu ions and Ca ions and effects of various chemical factors including the PH value. From the experimental and research results, the detection is shown unstable.

SUMMARY OF THE INVENTION

Accordingly, at least one object of this invention is to provide a silicon nanowire bio-chip structure and a manufacturing method thereof by forming an improved passivation layer structure on the silicon nanowire array surface, so as to make the silicon nanowire bio-chip uneasy to be polluted during preservation and use and stable in use.

To achieve the above purpose, the present invention provides a silicon nanowire bio-chip structure comprising: a semiconductor substrate, a $SiO_2$ insulating layer formed on the semiconductor substrate, a polysilicon layer formed on the $SiO_2$ insulating layer and a structural layer formed on the polysilicon layer; wherein, the polysilicon layer comprises a patterned silicon nanowire array; the structural layer includes a SiON layer, a TaN and/or $Ta_2O_5$ layer from bottom to top, the TaN and/or $Ta_2O_5$ layer only covers surface of each silicon nanowire in the silicon nanowire array.

According to the silicon nanowire bio-chip structure of the present invention, the thickness of the $SiO_2$ insulating layer is 1000 Å~5000 Å.

According to the silicon nanowire bio-chip structure of the present invention, the thickness of the polysilicon layer is 50 Å~1000 Å.

According to the silicon nanowire bio-chip structure of the present invention, the linewidth of the silicon nanowire is 5 nm~130 nm; the thickness of the silicon nanowire is 5 nm~100 nm.

According to the silicon nanowire bio-chip structure of the present invention, the thickness of the SiON layer is 10 Å~50 Å; the thickness of the TaN layer is 10 Å~50 Å; the thickness of the $Ta_2O_5$ layer is 10 Å~50 Å.

To achieve the above purpose, the present invention also provides a manufacturing method of a silicon nanowire bio-chip structure, the method comprises the following steps:

step S01: providing a semiconductor substrate;

step S02: forming a $SiO_2$ insulating layer on the semiconductor substrate;

step S03: forming a polysilicon layer on the $SiO_2$ insulating layer;

step S04: patterning the polysilicon layer to form a silicon nanowire array;

step S05: forming a structural layer on the silicon nanowire array, wherein the structural layer includes a SiON layer, a TaN and/or $Ta_2O_5$ layer from bottom to top;

step S06: removing the TaN and/or $Ta_2O_5$ layer between silicon nanowires in the silicon nanowire array.

According to the manufacturing method of the present invention, the $SiO_2$ insulating layer is formed by wet oxidation in the step S02.

According to the manufacturing method of the present invention, the silicon nanowire array is formed by dry etching in the step S04.

According to the manufacturing method of the present invention, the SiON layer is formed on the surface of the silicon nanowire array by thermal oxidation, and the TaN and/or $Ta_2O_5$ layer is formed by atomic layer deposition in the step S05.

According to the manufacturing method of the present invention, the TaN and/or $Ta_2O_5$ layer between the silicon nanowires are removed by plasma dry etching in the step S06.

From the technical solution mentioned above, according to the silicon nanowire bio-chip structure and the manufacturing method of the present invention, the structural layer is utilized as a protection layer which not only prevents the silicon nanowire (SiNW) array from being polluted during preservation and use, but also block the pollutants of Na ions, K ions, Fe ions, Cu ions and Ca ions as well as the effects of chemical factors including the PH value during biological detection even the bulk and solution of the samples are diversified, thereby achieving the high stability of detection.

DETAILED DESCRIPTION OF THE EMBODIMENTS

Reference will now be made in detail to the present preferred embodiments to provide a further understanding of the invention. The specific embodiments and the accompanying drawings discussed are merely illustrative of specific ways to make and use the invention, and do not limit the scope of the invention or the appended claims.

The silicon nanowire bio-chip structure and the manufacturing method thereof of the present invention will be described in further details hereinafter with respect to the embodiments and the accompany drawings FIG. 1 to FIG. 5.

Figure 1:
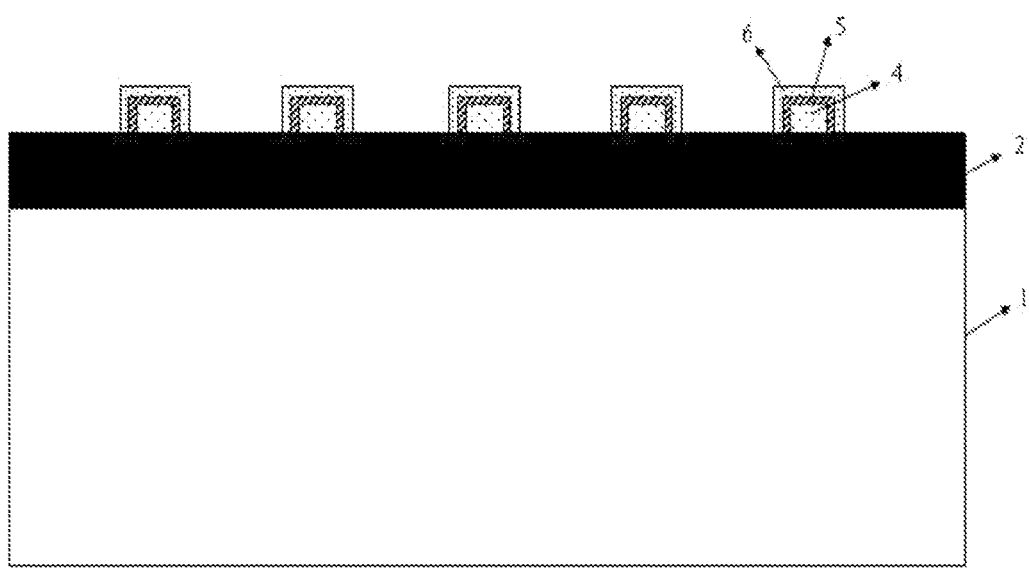
FIG. 1 is a sectional diagram of the silicon nanowire bio-chip structure in an embodiment of the present invention.

FIG. 1 is a sectional diagram of the silicon nanowire bio-chip structure in an embodiment. Referring to FIG. 1, the silicon nanowire bio-chip structure of the present invention is similar to the conventional silicon nanowire bio-chip. It comprises a semiconductor substrate 1, a $SiO_2$ insulating layer 2 formed on the semiconductor substrate, a polysilicon layer 3 having a patterned silicon nanowire array 4 formed on the $SiO_2$ insulating layer 2, and a structural layer.

The difference between the silicon nanowire bio-chip structure of the present invention and the conventional silicon nanowire bio-chip is that, as shown in FIG. 1, the structural layer includes, from bottom to top, a SiON layer 5, and a TaN and/or $Ta_2O_5$ layer. In the embodiment, the structural layer includes a SiON layer 5, and a TaN and $Ta_2O_5$ layer 6 from bottom to top. Wherein, the TaN and $Ta_2O_5$ layer 6 only covers the surface of each silicon nanowire in the silicon nanowire array. The SiON layer 5 is used as a passivation layer to reduce the surface activity of the silicon nanowire array so as to block the pollution and the effect of environmental factors such as PH value and humidity during the preservation and use of the bio-chip structure. The TaN and $Ta_2O_5$ layer 6 can prevent the silicon nanowire from being polluted by the spread Na ions and K ions.

Figure 2:
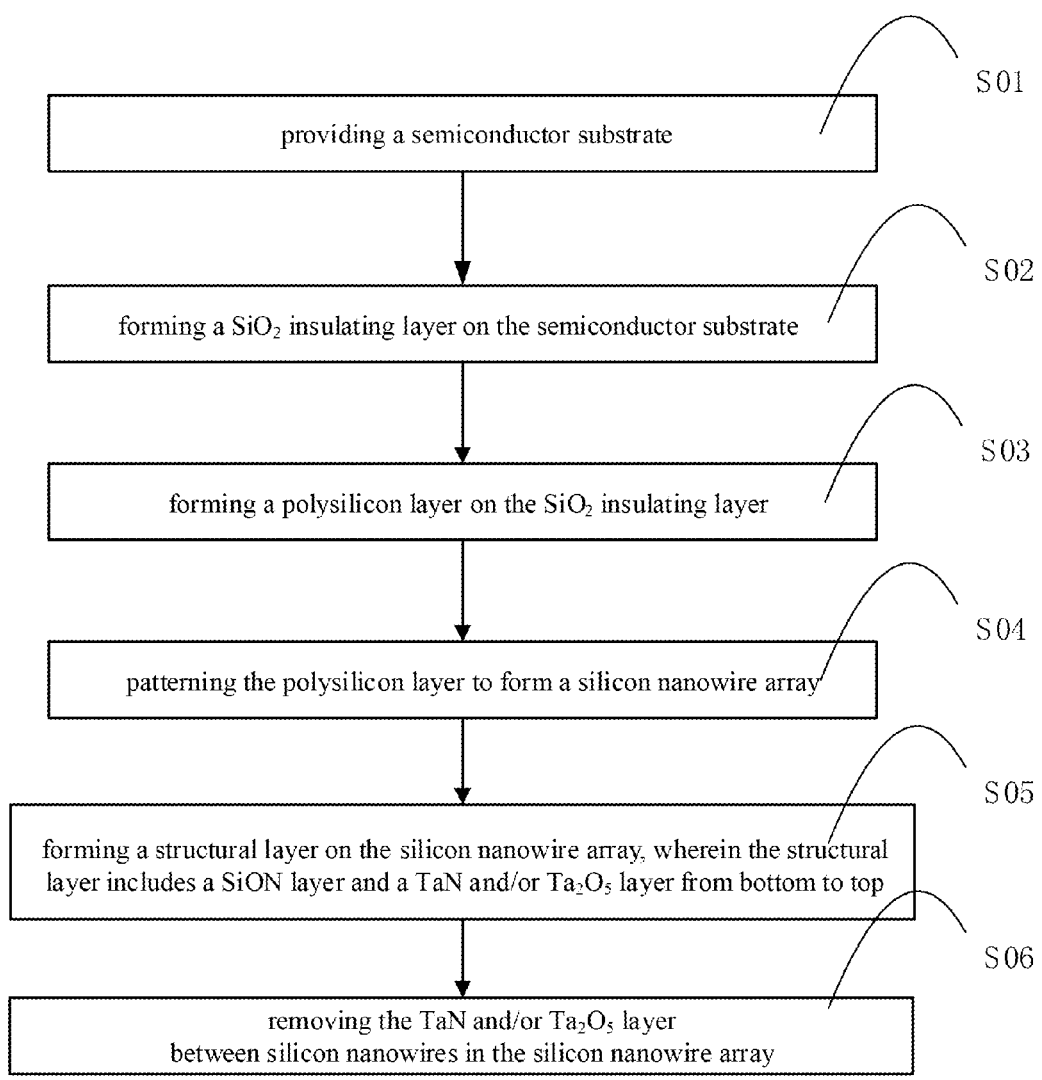
FIG. 2 is a flow chart of the manufacturing method of the silicon nanowire bio-chip structure in an embodiment of the present invention.

FIG. 2 is a flow chart illustrating the manufacturing method of the silicon nanowire bio-chip structure in an embodiment of the present invention. As shown in FIG. 2, in the embodiment of the present invention, the manufacturing method comprises the following steps:

step S01: providing a semiconductor substrate 1;

step S02: forming a $SiO_2$ insulating layer 2 on the semiconductor substrate;

step S03: forming a polysilicon layer 3 on the $SiO_2$ insulating layer;

step S04: patterning the polysilicon layer 3 to form a silicon nanowire array 4;

step S05: forming a structural layer having a certain thickness on the silicon nanowire array 4, wherein the structural layer includes a SiON layer 5, a TaN and $Ta_2O_5$ layer 6 from bottom to top;

step S06: removing the TaN and $Ta_2O_5$ layer 6 between silicon nanowires in the silicon nanowire array.

Figure 3:
FIGS. 3-5 are sectional diagrams of the silicon nanowire bio-chip structure illustrating the steps of the manufacturing method in FIG. 2.

FIG. 3 illustrates the structure of the silicon nanowire bio-chip formed after the steps S01, S02 and S03. As shown in FIG. 3, firstly, the $SiO_2$ layer 2 is formed on the semiconductor substrate 1 by wet oxidation, the thickness of the $SiO_2$ layer 2 is preferably to be 1000 Å~5000 Å; then, the polysilicon layer 3 is formed on the $SiO_2$ layer 2 in a furnace tube, the thickness of the polysilicon layer 3 can be 50 Å~1000 Å.

Figure 4:
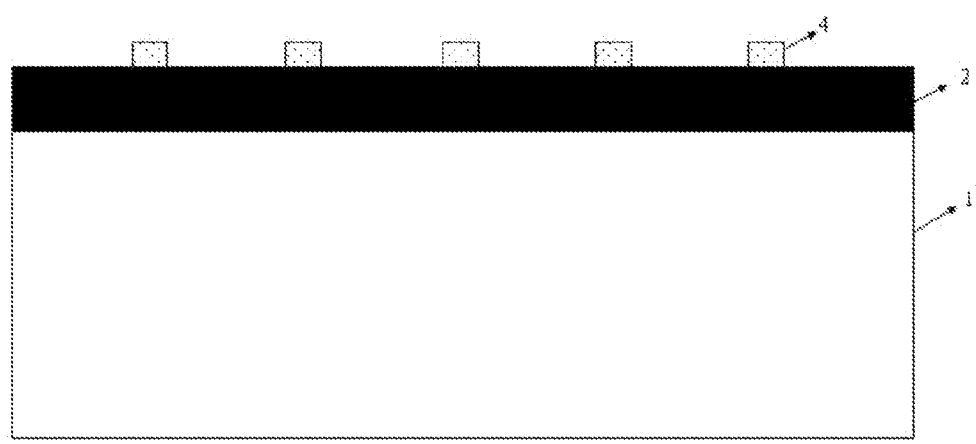

FIG. 4 illustrates the structure of the silicon nanowire bio-chip formed after the steps S04. As shown in FIG. 4, lithography and dry etching process is performed to the polysilicon layer 3 to form the silicon nanowire (SiNW) array 4. The linewidth of the silicon nanowires in the SiNW array 4 can be 5 nm~130 nm, the thickness of the silicon nanowires can be 5 nm~100 nm.

Figure 5:
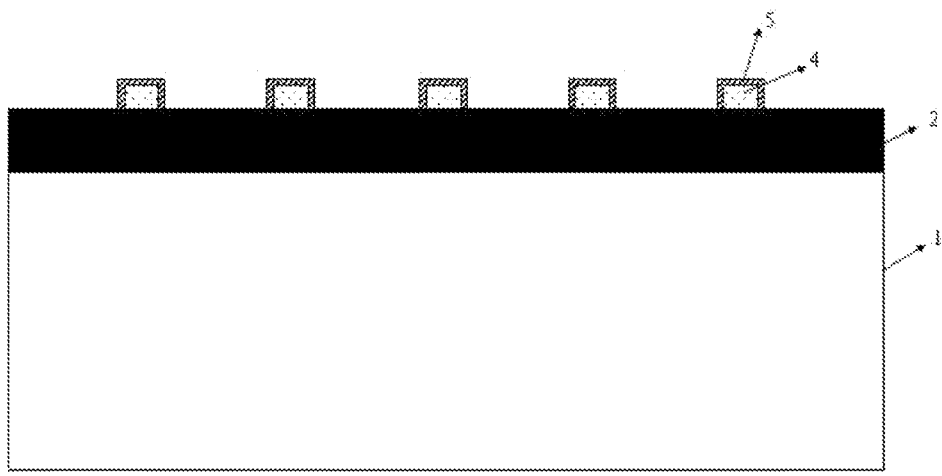

FIG. 5 illustrates the structure of the silicon nanowire bio-chip formed after the steps S05. As shown in FIG. 5, the SiON layer 5 is formed on the silicon nanowire array 4 by thermal oxidation, the thickness of the SiON layer 5 can be 10 Å~50 Å.

Please referring to FIG. 1, which illustrates the structure of the silicon nanowire bio-chip formed after the steps S06 and S07, in the embodiment, the TaN and $Ta_2O_5$ layer 6 is formed by atomic layer deposition, then the TaN and $Ta_2O_5$ layer 6 between the silicon nanowires is removed by plasma dry etching. The thickness of the TaN layer can be 10 Å~50 Å; the thickness of the $Ta_2O_5$ layer can be 10 Å~50 Å. In the embodiment, the TaN layer can also be used as a etch stop layer.

In conclusion, according to the silicon nanowire bio-chip structure and the manufacturing method of the present invention, the silicon nanowire array is prevented from being polluted during preservation and use, and the pollutants of Na ions, K ions, Fe ions, Cu ions and Ca ions as well as the effects of chemical factors including PH value are blocked during biological detection even the bulk and solution of the samples are diversified, thereby achieving the high stability of detection.

Although the present invention has been disclosed as above with respect to the preferred embodiments, they should not be construed as limitations to the present invention. Various modifications and variations can be made by the ordinary skilled in the art without departing the spirit and scope of the present invention. Therefore, the protection scope of the present invention should be defined by the appended claims.

The invention claimed is:

1. A silicon nanowire bio-chip structure comprising:
a semiconductor substrate;
a $SiO_2$ insulating layer formed on the semiconductor substrate;
a polysilicon layer having a patterned silicon nanowire array formed on the $SiO_2$ insulating layer; wherein, the silicon nanowire bio-chip structure further comprises:
a structural layer formed on the polysilicon layer; wherein the structural layer includes from bottom to top a SiON layer for reducing surface activity of the silicon nanowire array, a TaN and $Ta_2O_5$ layer for blocking ionic pollutants, the TaN and $Ta_2O_5$ layer only completely covers surfaces of each silicon nanowire in the silicon nanowire array.

2. The silicon nanowire bio-chip structure according to claim 1, wherein the thickness of the $SiO_2$ insulating layer is 1000 Å~5000 Å.

3. The silicon nanowire bio-chip structure according to claim 1, wherein the thickness of the polysilicon layer is 50 Å~1000 Å.

4. The silicon nanowire bio-chip structure according to claim 1, wherein the linewidth of the silicon nanowire is 5 nm~130 nm; the thickness of the silicon nanowire is 5 nm~100 nm.

5. The silicon nanowire bio-chip structure according to claim 1, wherein the thickness of the SiON layer is 10 Å~50 Å; the thickness of a TaN layer of the TaN and $Ta_2O_5$ layer is 10 Å~50 Å; the thickness of a $Ta_2O_5$ layer of the TaN and $Ta_2O_5$ layer is 10 Å~50 Å.

* * * * *